(12) United States Patent
Lin

(10) Patent No.: US 12,208,292 B2
(45) Date of Patent: Jan. 28, 2025

(54) NASAL MASK AND ASSOCIATED FILTER

(71) Applicant: Carol Chia Yuan Lin, Klamath Falls, OR (US)

(72) Inventor: Carol Chia Yuan Lin, Klamath Falls, OR (US)

( * ) Notice: Subject to any disclaimer, the term of this patent is extended or adjusted under 35 U.S.C. 154(b) by 347 days.

(21) Appl. No.: 17/912,534

(22) PCT Filed: Mar. 15, 2021

(86) PCT No.: PCT/US2021/022374
§ 371 (c)(1),
(2) Date: Sep. 19, 2022

(87) PCT Pub. No.: WO2021/206865
PCT Pub. Date: Oct. 14, 2021

(65) Prior Publication Data
US 2023/0173311 A1   Jun. 8, 2023

Related U.S. Application Data

(60) Provisional application No. 63/151,476, filed on Feb. 19, 2021.

(30) Foreign Application Priority Data

| Apr. 8, 2020 | (TW) | ................................ | 109204032 |
| Apr. 27, 2020 | (TW) | ................................ | 109205023 |
| Apr. 27, 2020 | (TW) | ................................ | 109205024 |

(51) Int. Cl.
*A62B 23/06* (2006.01)
*A61M 16/06* (2006.01)
(52) U.S. Cl.
CPC ......... *A62B 23/06* (2013.01); *A61M 16/0688* (2014.02)

(58) Field of Classification Search
CPC ....... A62B 23/06; A62B 23/00; A62B 23/025; A62B 18/084; A62B 7/10; A62B 9/04; A62B 9/06; A61M 16/0688
See application file for complete search history.

(56) References Cited

U.S. PATENT DOCUMENTS 390,027 A * 9/1888 Locke ............... A61M 16/0666
128/206.13
3,451,392 A * 6/1969 Cook ..................... A62B 23/06
55/DIG. 35

(Continued)

FOREIGN PATENT DOCUMENTS

| CN | 2046022 U | * 10/1989 |
| CN | 1119549 A | 4/1996 |

(Continued)

OTHER PUBLICATIONS

WoodyKnows Super Defense Nose Nasal Filters (New Model) Reduce Pollen, Dust, Dander, and Mold Allergens Allergy, Air Pollution PM2.5(3 Filter Frames and 6 Pairs of Replacement Filters)(I-S/II-S/III-S), access: https://www.amazon.in/WoodyKnows-Model-Allergens-Pollution-Replacement/dp/B00SHELUN2.

(Continued)

*Primary Examiner* — Colin W Stuart
(74) *Attorney, Agent, or Firm* — Daylight Law, P.C.

(57) ABSTRACT

A nasal mask and associated nasal septum holder and nasal mask filter are disclosed. The nasal mask includes a clamping body with a pair of clamping arms. The clamping body and the pair of clamping arms are shaped to surround a nasal septum. The nasal mask further includes a holding feature attached to the clamping body and a filter with a pocket. The filter is shaped to cover a front end of a nose when the holding feature is attached to the pocket.

37 Claims, 11 Drawing Sheets

(56) References Cited

U.S. PATENT DOCUMENTS

| | | | |
|---|---|---|---|
| 4,004,584 A | 1/1977 | Geaney | |
| 5,392,773 A | 2/1995 | Bertrand | |
| D461,890 S * | 8/2002 | Lawrence | D24/106 |
| 6,701,924 B1 | 3/2004 | Land, Jr. et al. | |
| 2005/0161046 A1 | 7/2005 | Michaels | |
| 2006/0150980 A1 | 7/2006 | Kim | |
| 2008/0087286 A1 | 4/2008 | Jones | |
| 2010/0331777 A1 | 12/2010 | Danielsson | |
| 2017/0157437 A1 | 6/2017 | Krespi et al. | |
| 2019/0374797 A1 | 12/2019 | Jones | |

FOREIGN PATENT DOCUMENTS

| | | | |
|---|---|---|---|
| CN | 2375333 Y | 4/2000 | |
| CN | 201815013 U | 4/2011 | |
| CN | 102462899 A | 5/2012 | |
| CN | 202459895 U | 10/2012 | |
| CN | 212233235 U | 12/2020 | |
| DE | 4333853 A1 | 4/1994 | |
| EP | 2903699 A1 | 8/2015 | |
| FR | 738520 A | 12/1932 | |
| JP | 2008188367 A | 8/2008 | |
| JP | 4555386 B1 * | 9/2010 | |
| JP | 2010279603 A | 12/2010 | |
| KR | 2019960033588 U | 11/1996 | |
| KR | 970002309 Y1 | 1/1997 | |
| KR | 1020080029957 A | 4/2008 | |
| KR | 1020160040066 A | 4/2016 | |
| KR | 20160135568 A * | 11/2016 | |
| KR | 1020160135568 A | 11/2016 | |
| KR | 101960752 B1 | 3/2019 | |
| KR | 101969677 B1 | 4/2019 | |
| TW | M572769 U | 1/2019 | |
| TW | M593883 U | 4/2020 | |
| TW | M607819 U | 2/2021 | |
| WO | WO-2020022632 A1 * | 1/2020 | A62B 23/06 |
| WO | 2021206865 A1 | 10/2021 | |

OTHER PUBLICATIONS

Adreco Plastics. ,Polypropylene uses, Dec. 20, 2018 (Dec. 20, 2018), http://www.adrecoplastics.co.uk/polypropylene-uses-applications/.

International Search Report dated Jun. 9, 2021 from International Application No. PCT/US2021/022374, 16 pages.

First Office Action from Chinese Application No. 202180001910X, dated Dec. 15, 2022, 10 pages.

International Preliminary Report on Patentability from International Application No. PCT/US2021/022374 dated Oct. 6, 2022, 9 pages.

* cited by examiner

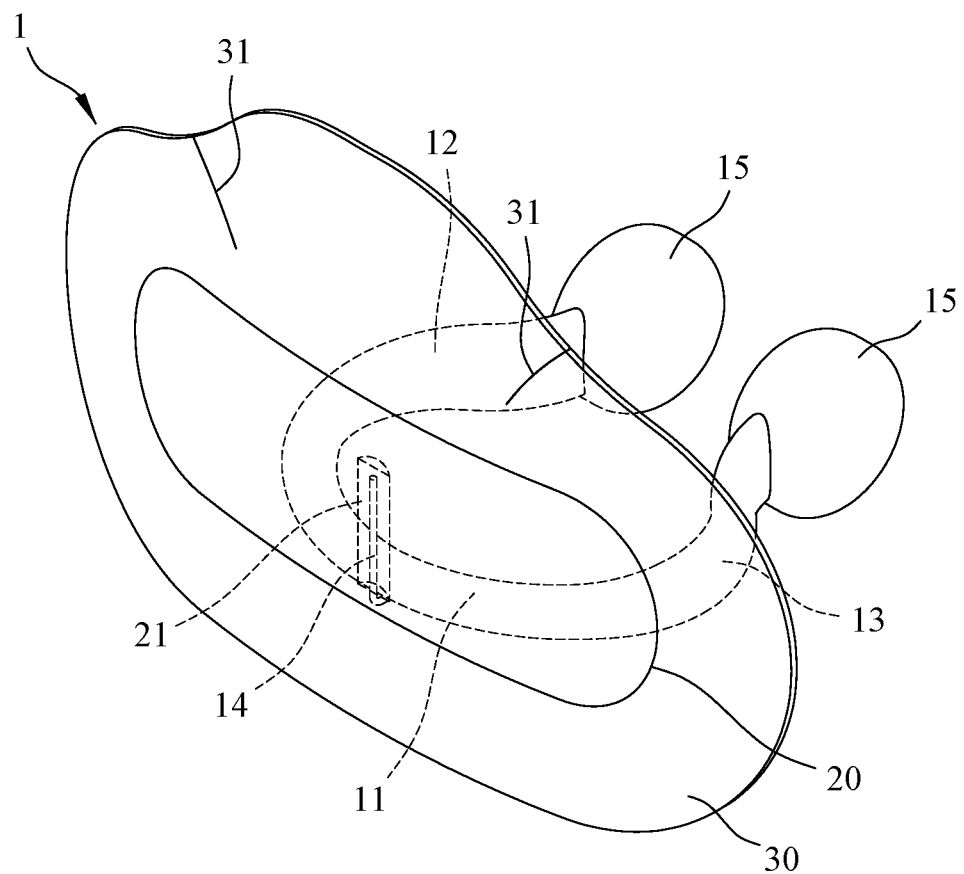
【FIG. 1A】
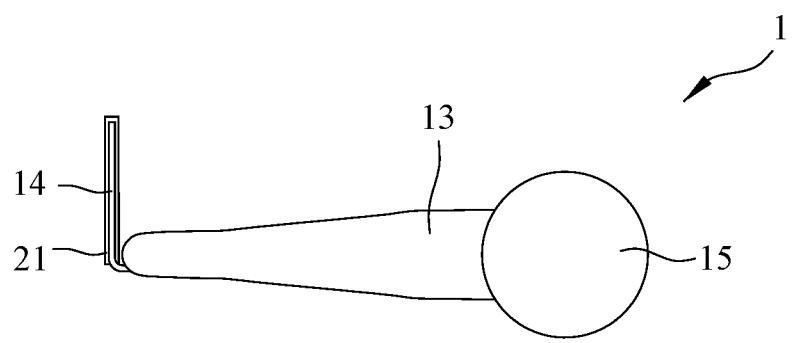
【FIG. 1B】

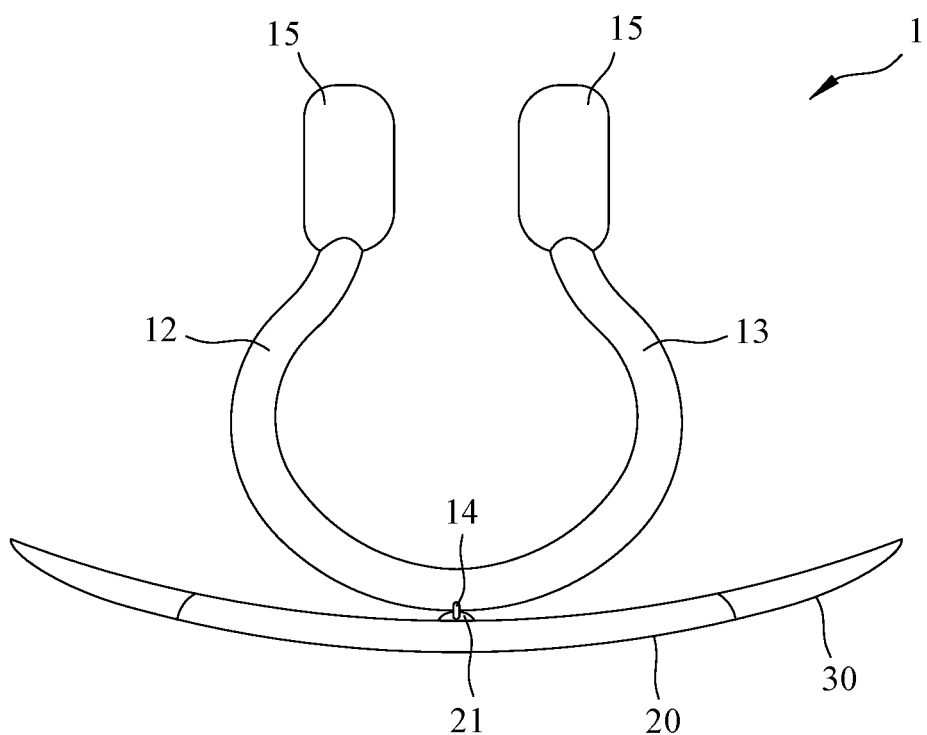
【FIG. 2】

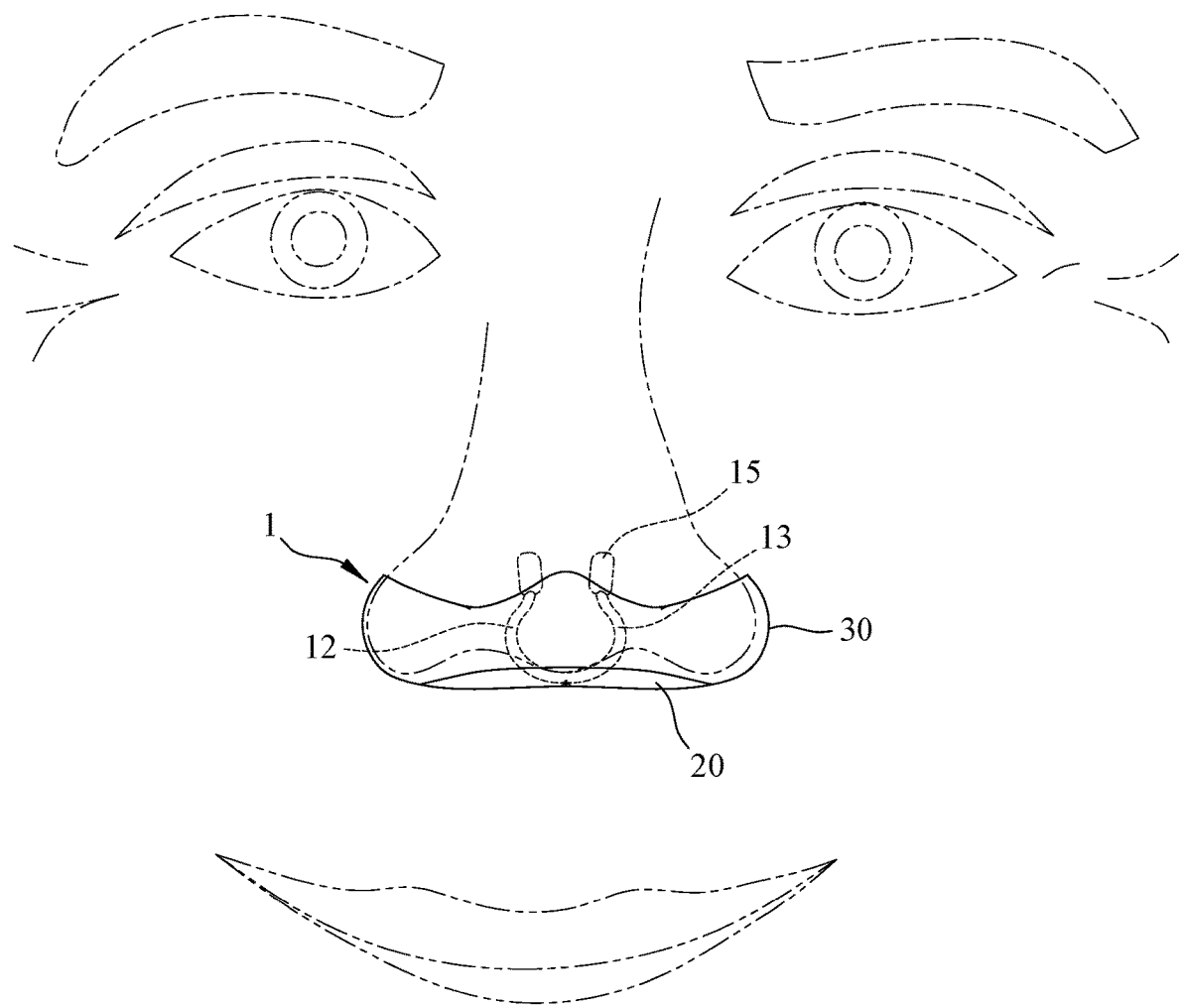
[FIG 3]

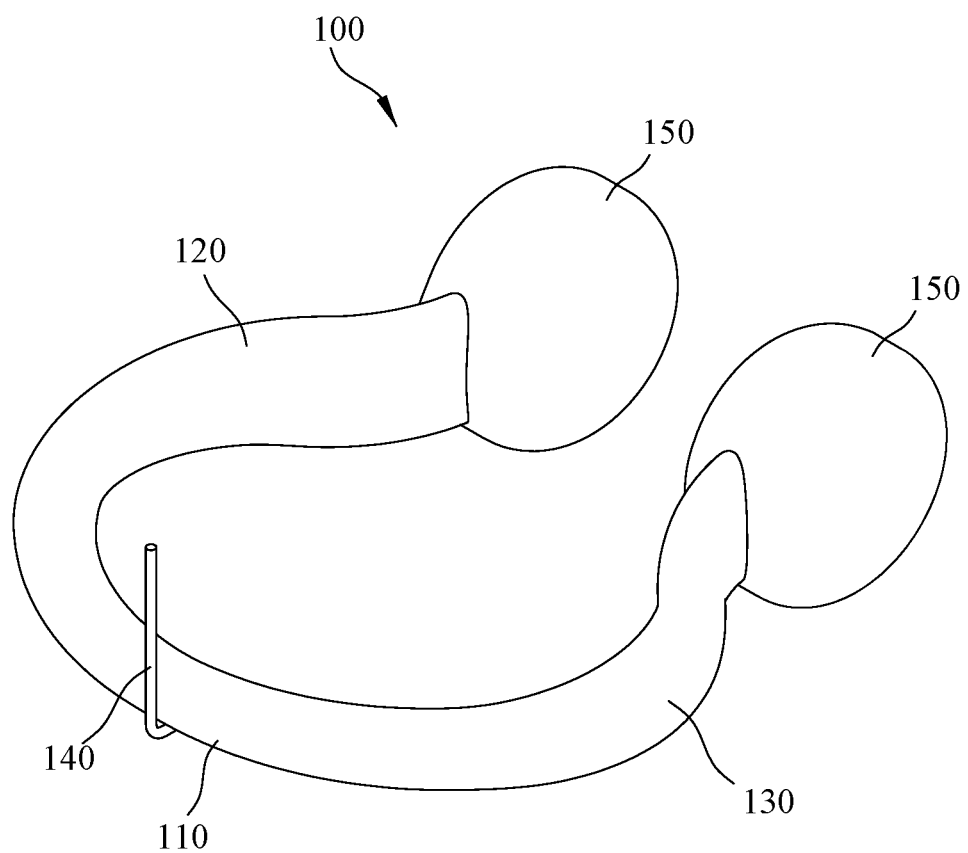
【FIG. 4】

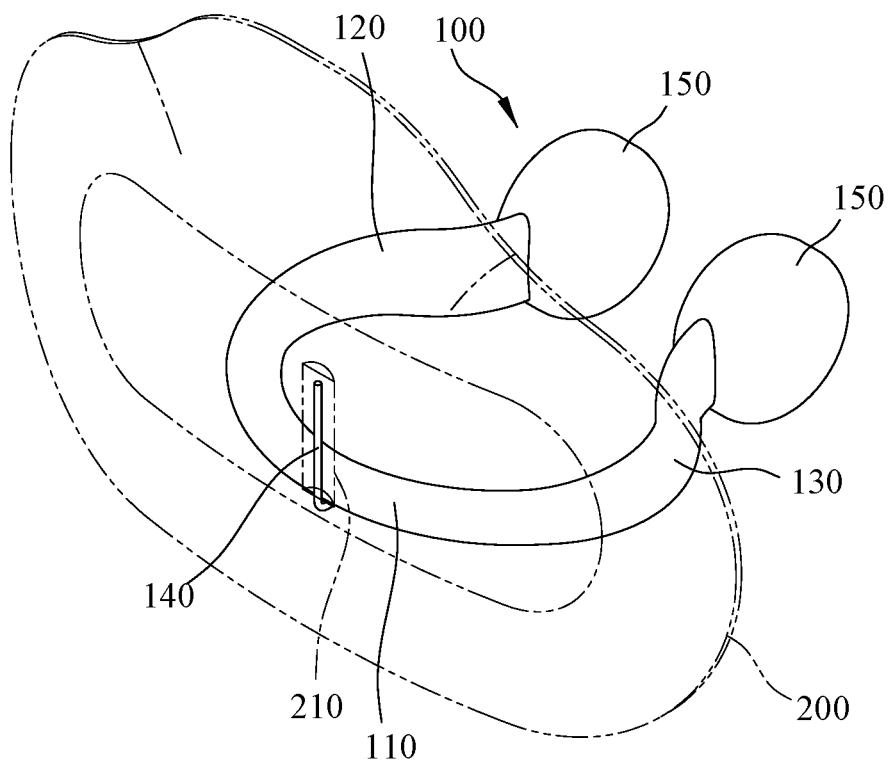
【FIG. 5A】
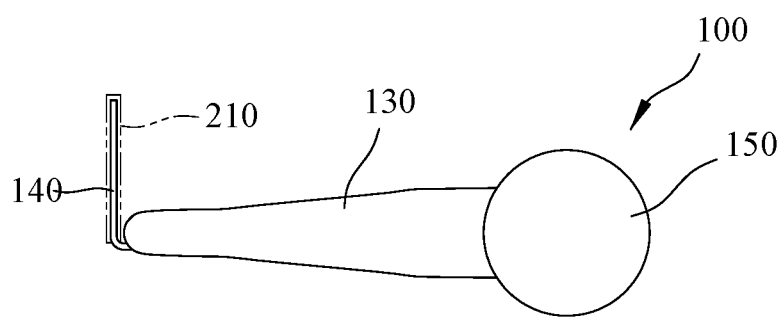
【FIG. 5B】

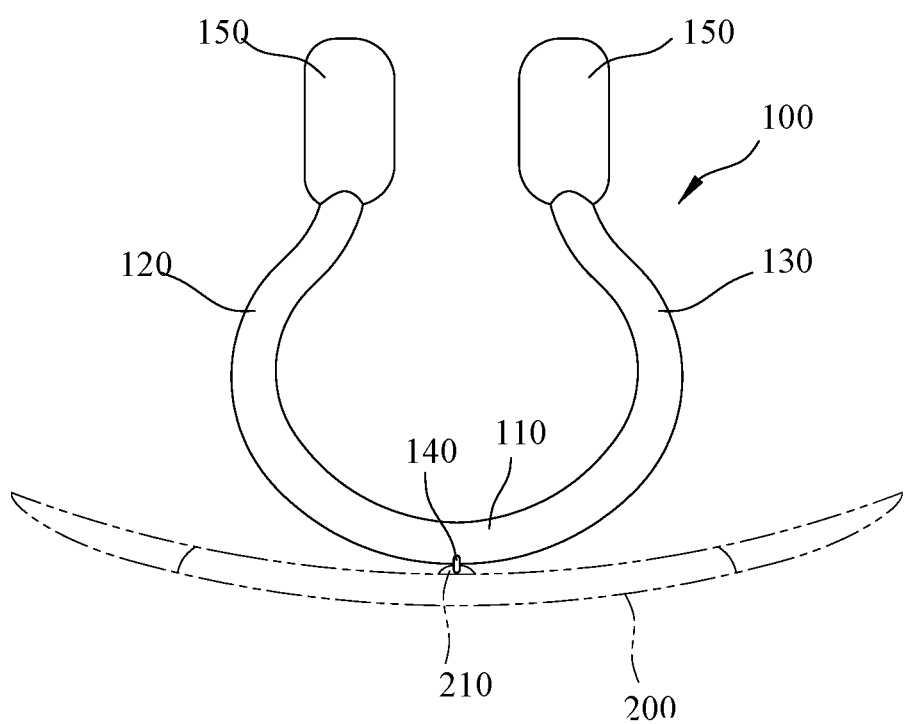
[FIG. 6]

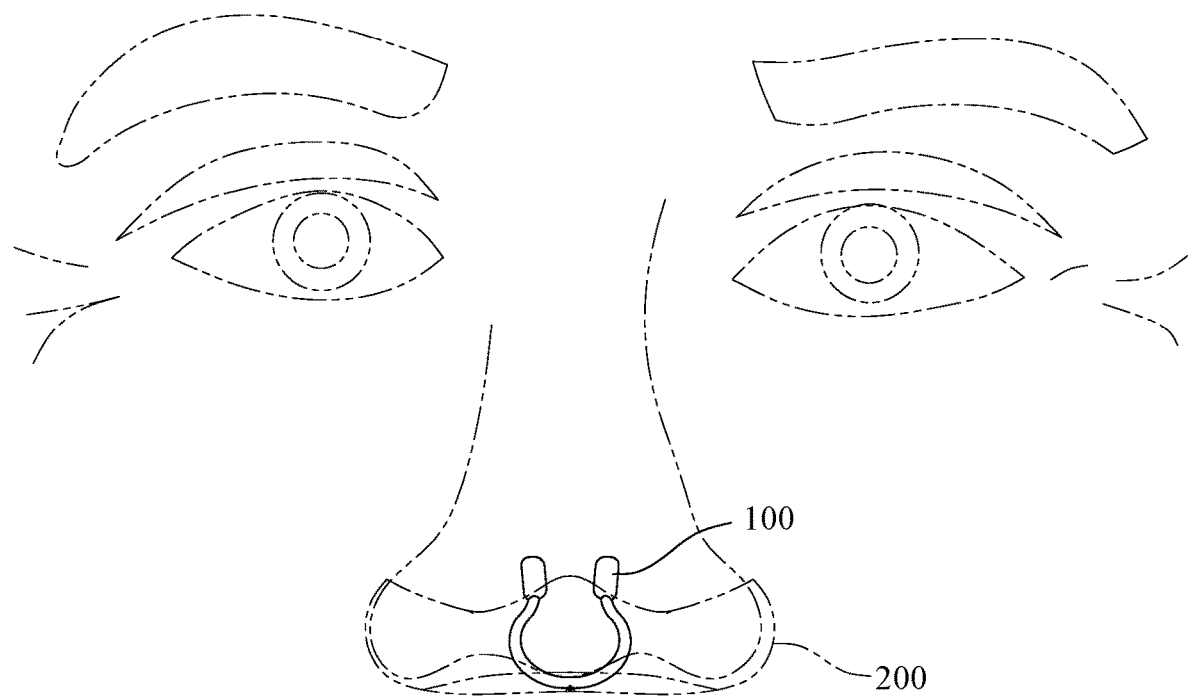

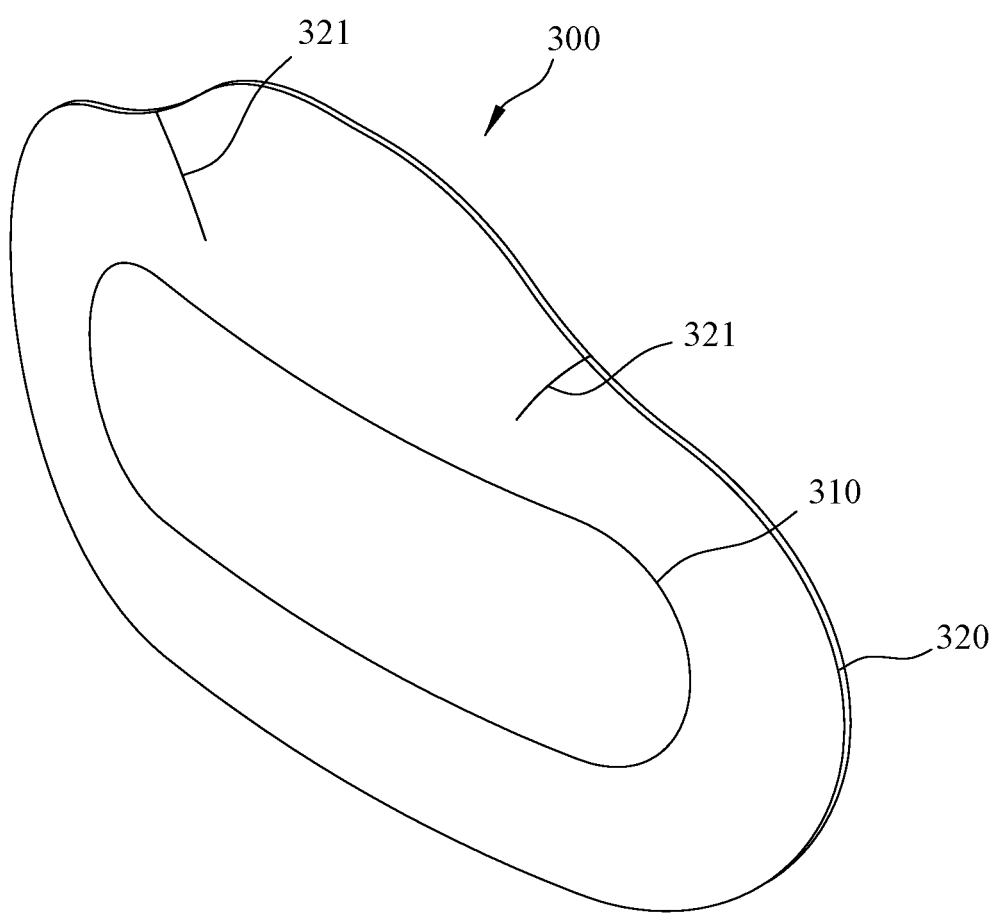
【FIG. 8】

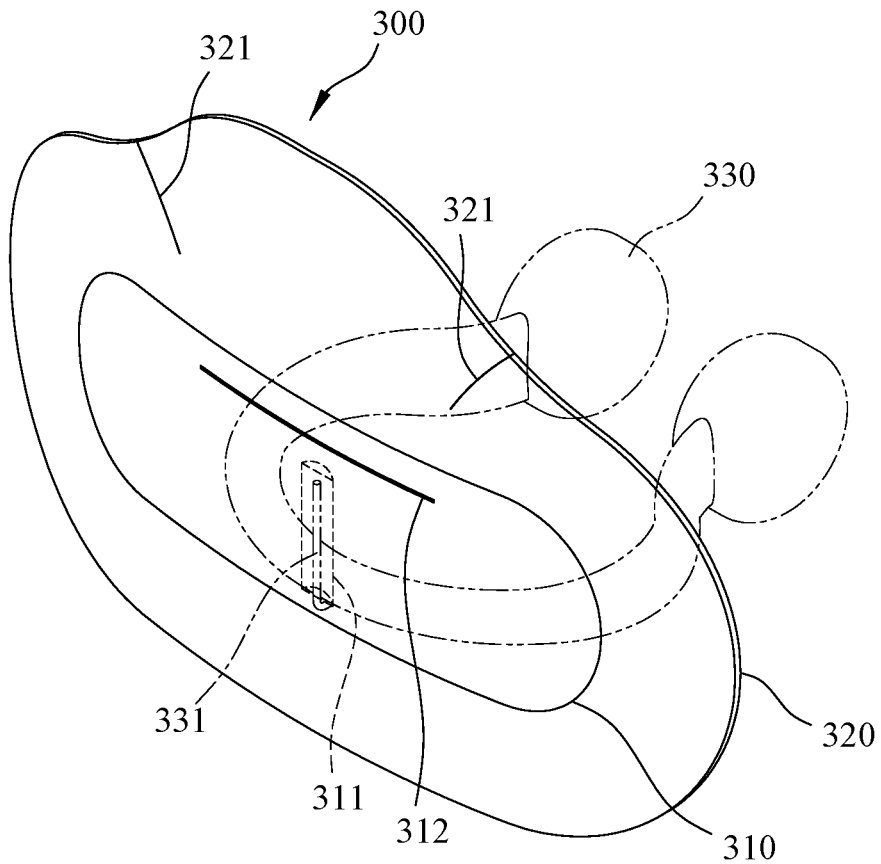
【FIG. 9A】
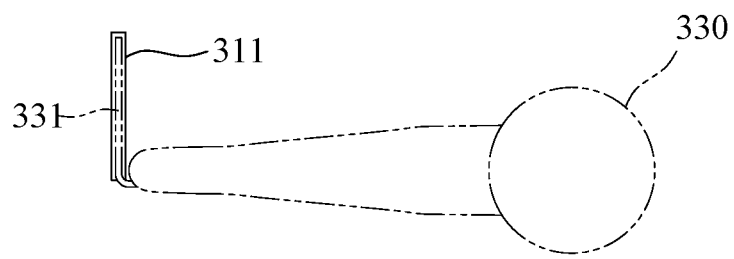
【FIG. 9B】

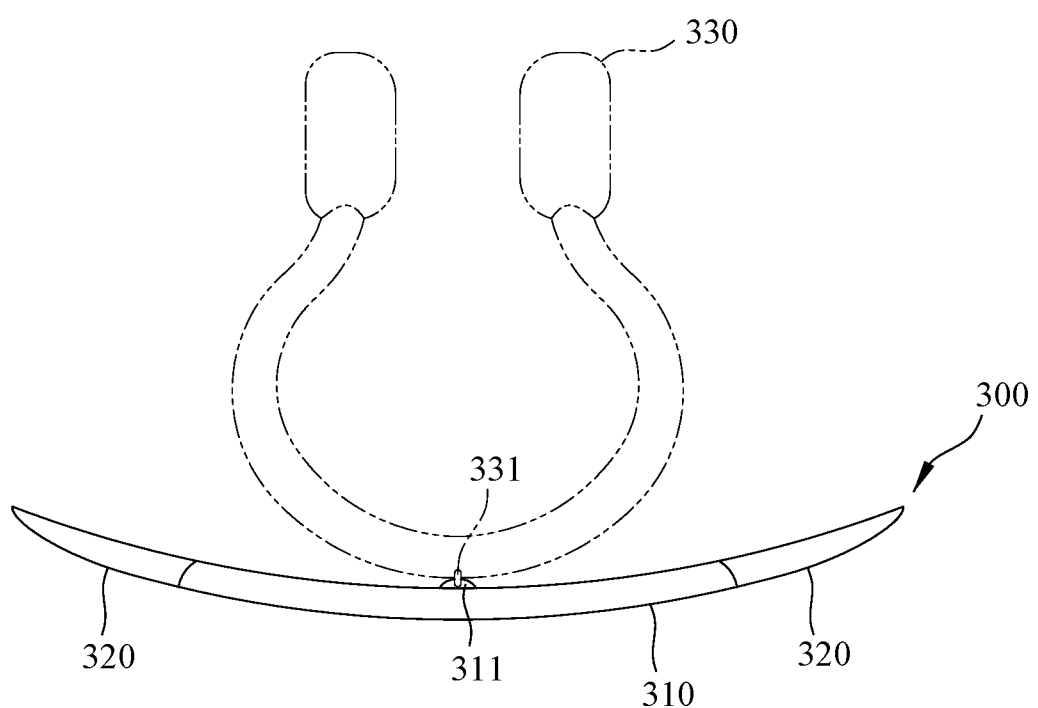
[FIG. 10]

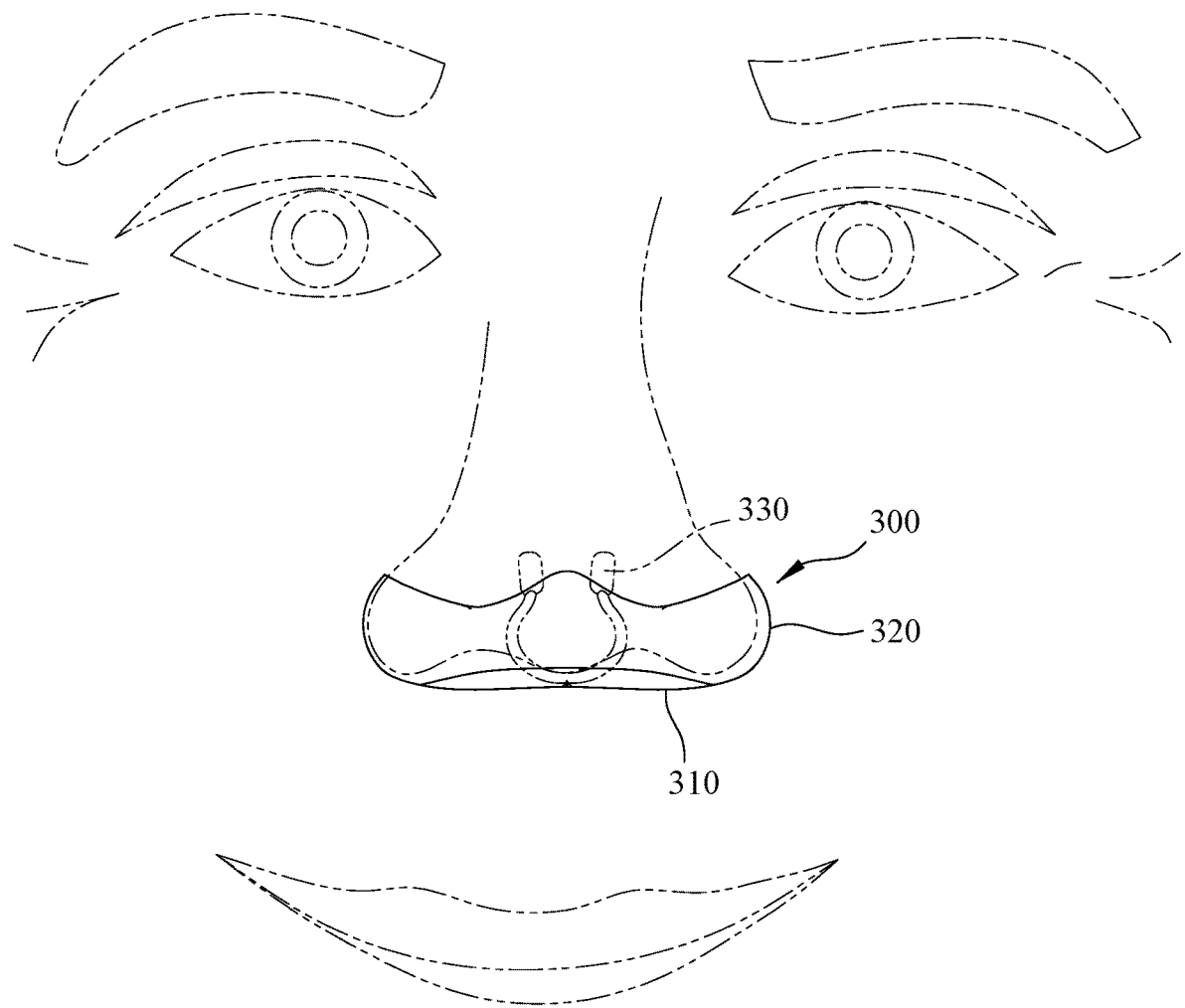
[FIG. 11]

NASAL MASK AND ASSOCIATED FILTER

CROSS REFERENCE TO RELATED APPLICATIONS

This application is a 35 U.S.C. § 371 National Stage of International Application No. PCT/US2021/022374, filed Mar. 15, 2021, which claims the benefit of U.S. Provisional Patent Application No. 63/151,476, filed on Feb. 19, 2021, which is incorporated by reference herein its entirety for all purposes, and claims priority to Taiwanese Patent Application No. 109204032 filed on Apr. 8, 2020, Taiwanese Patent Application No. 109205023 filed on Apr. 27, 2020, and Taiwanese Patent Application No. 109205024 filed on Apr. 27, 2020, all of which are incorporated by reference herein in their entirety for all purposes.

BACKGROUND

People use masks to filter harmful substances from the air such as pollutants, allergens, pathogens. However, common face masks are large and require multiple straps making the cost of materials and manufacturing and transportation higher than necessary. Also, because the mask covers half of a wearer's face, not only does it affect the aesthetics and social perception of the wearer, but it is also not convenient for daily activities involving the wearer's mouth such as giving verbal instructions, orders, or speeches, singing, performance art, eating, or drinking. Masks can also fog up glasses and cause the accumulation of moisture on the face of the wearer. Current masks are also easily affected in a deleterious manner by the contours of the face, which makes it difficult to achieve good air tightness during use. They are also loosely strapped to the ears, so that they often shift position after initial placement which results in reduced hermeticity even if they were initially placed correctly on the wearer's face. Furthermore, when people need to talk or eat, they often push the mask to their chins or let it dangle on the side, which gives the mask an opportunity to wipe their face and be contaminated. In these situations, once the mask is placed back in position, the contaminants will almost certainly be inhaled as the mask is now keeping the contaminants inside the interior hermetic volume of the mask. Finally, tightly worn masks, especially medical hard-shell masks, can leave indentations or even bruises on the face of the wearer and are uncomfortable.

Some approaches which address the aforementioned problems utilize nasal filters which are stuffed inside the nostrils of the wearer. These approaches improve portability and aesthetics. However, they are not easy to wear for a prolonged period because they are highly invasive. Furthermore, since the filters are fully stuffed inside the nostrils, the membrane close to the entrance of the nostrils is exposed to pollutants and pathogens. As such, it is difficult for this style of protective gear to completely prevent the nasal cavity from being exposed to harmful substances. Additionally, this style of protective gear can interfere with respiration and has a tendency to fall out of place, or off entirely, when the wearer exhales.

SUMMARY

The development of a lightweight filter mask that has high fixability and is small, convenient to wear, and easy to carry is important for both improving the experience of individual wearers as well as increasing the rate of overall public usage. Specific embodiments of the invention disclosed herein address these important objectives.

Specific embodiments of this invention refer to a nasal mask, especially a lightweight filtering nasal mask that only covers the nose of the user. Specific embodiments of this invention refer to a nasal septum holder, especially a nasal septum holder with a holding feature (e.g., a holding pin) for installing a nasal mask filter. Specific embodiments of this invention refer to a nasal mask filter, especially a nasal mask filter that covers the front portion of the wearer's nose including both nostrils and the surrounding skin. As used herein, the term "front end of the nose" refers to an anatomical collection of features of a human or animal nose which includes the tip of the nose, the wings of the nose, the front end of the nasal septum, and the nostril. In specific embodiments, the nasal mask filter can be a disposable filter that is attached to the holding feature of the nasal septum holder temporarily while the nasal mask is in use and is replaced between usages.

In specific embodiments of the invention, a nasal mask is provided. The nasal mask comprises a clamping body with a pair of clamping arms. The clamping body and the pair of clamping arms are shaped to surround a nasal septum. The nasal mask further comprises a holding feature attached to the clamping body and a filter with a pocket. The filter is shaped to cover a front end of a nose when the holding feature is attached to the pocket.

In specific embodiments of the invention, a nasal septum holder for a nasal mask is provided. The nasal septum holder comprises a clamping body and a pair of clamping arms. The clamping body and the pair of clamping arms are shaped to surround a nasal septum. The nasal septum holder further comprises a holding feature attached to the clamping body. The holding feature is shaped to attach to a pocket in a filter.

BRIEF DESCRIPTION OF THE DRAWINGS

FIG. 1A is a perspective view of a nasal mask according to an embodiment of the present invention.

FIG. 1B is a side view of a nasal mask according to an embodiment of the present invention.

FIG. 2 is a top view of a nasal mask according to an embodiment of the present invention.

FIG. 3 is an illustration of how specific embodiments of this invention can be used by a wearer.

FIG. 4 is a three-dimensional view of a nasal septum holder according to an embodiment of the invention.

FIG. 5A is a three-dimensional view of a nasal mask including a nasal mask filter attached to a nasal septum holder according to an embodiment of the present invention.

FIG. 5B is a side view of the nasal mask of FIG. 5A.

FIG. 6 is a top view of the nasal mask of FIG. 5A.

FIG. 7 is an illustration of how the nasal mask of FIG. 5A can be used by a wearer.

FIG. 8 is a three-dimensional view of a nasal mask filter with slits according to an embodiment of the invention.

FIG. 9A is a three-dimensional view of a nasal mask including a nasal mask filter, with a vent, attached to a nasal septum holder according to an embodiment of the present invention.

FIG. 9B is a side view of the nasal mask of FIG. 9A.

FIG. 10 is a top view of the nasal mask filter of FIG. 9A.

FIG. 11 is an illustration of how the nasal mask of FIG. 9A can be used by a wearer.

DETAILED DESCRIPTION

Nasal masks and associated filters in accordance with the summary above are disclosed in detail herein. The nasal masks and filters disclosed in this section are nonlimiting embodiments of the invention, are provided for explanatory purposes only, and should not be used to constrict the full scope of the invention. It is to be understood that the disclosed embodiments may or may not overlap with each other. Thus, part of one embodiment, or specific embodiments thereof, may or may not fall within the ambit of another, or specific embodiments thereof, and vice versa. Different embodiments from different aspects may be combined or practiced separately. Many different combinations and sub-combinations of the representative embodiments shown within the broad framework of this invention, that may be apparent to those skilled in the art but not explicitly shown or described, should not be construed as precluded.

In specific embodiments, the disclosed nasal masks exhibit significant benefits. The nasal masks are both small and lightweight, have a high degree of fixation, and maintain the aesthetic and convenience of an uncovered human face. As such, in specific embodiments the nasal masks disclosed herein can be worn even while engaging in day-to-day activities such as eating, singing, speaking, sleeping, and seeing a dentist. The nasal mask can therefore be appealing to people who need to access their mouth in public spaces such as restaurant customers and dental patients, and people who need to give clear verbal orders such as military officers, public speakers, choir singers, and other performers. Furthermore, in specific embodiments the nasal mask can filter the air inhaled into the nasal cavity while keeping the nasal cavity moist so that it improves the protection of the respiratory tract. Furthermore, in specific embodiments, the nasal mask does not obstruct facial recognition, which makes passing customs, borders, getting photographed for a license or identification card, using biometric facial recognition logins, or being recognized by on old friend on the street, much easier.

With specific reference to nasal masks used to prevent the inhalation of pathogens, it has been found that the nasal cavity is the dominant initial site from which lung infections tend to be seeded. As such, masks that protect the nasal cavity and therapeutic strategies such as nasal irrigation or antiviral/antibacterial nasal sprays can significantly reduce the rate of infection for upper respiratory infections. At the same time, nasal filters which are placed wholly within the nostrils exhibit relative drawbacks when compared to specific nasal masks disclosed herein because the nasal masks disclosed herein allow the nasal cavity to remain moist and therefore less amenable to the hosting of initial infection sites.

In specific embodiments, the disclosed nasal filters exhibit significant benefits. For example, in specific embodiments of the invention, the disclosed nasal masks utilize a replaceable filter to improve the hygienic utility of the mask and the practicality of its use. Additionally, in specific embodiments of the invention the nasal mask is much smaller than a standard face mask which reduces the environmental footprint and transportation costs of the mask as compared to alternative options. If the only portion of the mask which is discarded is a small filter only large enough to cover the front of a wearer's nose, these benefits are even more pronounced.

The disclosed nasal masks can include a nasal septum holder. The nasal septum holder can be any structure that can be secured to the nasal septum of a wearer. The nasal septum holder can be configured to not interfere with facial movements and maintain the aesthetic appearance of an unmasked person. The nasal septum holder can include a holding feature to secure a nasal mask filter to the nasal septum holder. The nasal septum holder can be a clamping body. The clamping body can have two arms bent backward toward each other to form an arc and a front middle section with a holding feature perpendicular to the two arms. The holding feature can be a holding pin and be used to attach to a nasal filter as described below. The two arms of the clamping body can be a right clamping arm and a left clamping arm. The right clamping arm and the left clamping arm can be in an inclined arc shape to provide the clamping body with elasticity. The material of the clamping body can be elastic to provide a comfortable fit against the septum of the wearer. In specific embodiments, the clamping body further has a protrusion such as a pad, a contour, or another shape located at the ends of the two arms to prevent slipping, to increase friction, and to reduce pressure at a contact surface to provide a comfortable fit.

The disclosed nasal masks can include a holding feature. The holding feature can be configured to hold the nasal filter to the nasal septum holder. The holding feature can be a cantilever, protrusion, platform, or pin configured to attach to the nasal filter. The holding feature can be configured to attach to a pocket (e.g., a tube with openings on two sides or a pouch with an opening on one side) on a nasal filter (e.g., by having the cantilever extend into the pocket). The holding feature can be located at the front middle section of the nasal septum holder. The holding feature can be a cantilever extending out from the main arc, or other main plane depending upon the shape, of the nasal septum holder. The holding feature can be used to increase the fixation of the nasal filter covering the opening of a wearer's nostrils. The holding feature can allow wearers to freely and easily disassemble and assemble a nasal mask by attaching and removing a nasal mask filter from the nasal septum holder. The holding feature could alternatively comprise any fastening means such as buttons, snaps, hook and loop fasteners, or adhesives. The fastening means could be configured to attach to corresponding means on the nasal filter. In alternative embodiments, the nasal septum holder can be used in conjunction with other face masks when necessary. In alternative embodiments, the features described as being located on the nasal septum holder and serving as a holding feature can be switched with the features described as being located on the filter and serving to be held by the holding feature. For example, the filter can include an attached cantilever extension and the nasal septum holder can include a pocket to receive the cantilever.

The holding feature can be configurable relative to the nasal septum holder. In specific embodiments mentioned above, the holding feature may be perpendicular to and extending away from the main plane of the nasal septum holder. As a result, the volume required to package and transport the combined holding feature and nasal septum holder may be unnecessarily large. To avoid this issue, and to generally decrease the cost of mass distribution of the nasal masks disclosed herein, and to increase the convenience of carrying the nasal masks disclosed herein to an individual wearer, the holding feature can be configurable relative to the nasal septum holder to decrease the dimensions of the combined device. For example, the holding feature could be detachably attached to the nasal septum holder or it could be rotatable relative to the nasal septum holder. An example of a detachably attached holding feature would be one with a shaped joint for forming a friction or negative clearance mechanical bond with a corresponding formation on the nasal septum holder. The shaped joint could include an extension, a prehensile tension joint, screw heads, or a mechanical keying arrangement to snap, screw, or otherwise connect the holding feature with the nasal septum holder. In these examples, the combined nasal septum holder and holding feature could be transported as separate pieces and could then be connected when the nasal mask was ready for use. As another example, the holding feature could be connected to the nasal septum holder using a rotatable joint such that the holding feature could be folded out and away from a main plane of the nasal septum holder when the device was becoming ready for use. The rotatable joint could be a one way rotating joint or a one-way biased rotating joint that would snap or otherwise stick in an open position after the joint was opened. Using these approaches the overall nasal mask could keep a low-profile during transport, but sill exhibit the benefits of embodiments of the invention disclosed herein.

The disclosed nasal masks can be associated with a nasal filter. The filter can be a replaceable filter. The filter can include a filter sheet to filter air flowing through the filter by trapping pollutants, allergens, and pathogens in the air as it moves through the filter sheet. The filter can be configured to cover both nostrils and the skin around and over the nostrils. Specific embodiments of the invention refer to a nasal mask filter, which has the characteristics of small size, low interference, and high fixation. The design of the nasal mask filter is both discreet and functional, which increases the continuous usage time, so that, it greatly increases the people's willingness to use the nasal mask filter. The nasal mask filter can be easily changed to maintain hygiene. Because of its size, it reduces the waste of filter materials and it is easy to carry. The nasal mask filter can be used by itself or in conjunction with other facial masks if necessary. For example, the filter could be used in combination with a full facial mask covering both the nose and mouth.

The nasal mask filter can be configured to be secured to an associated nasal septum holder. The nasal mask filter can be configured to attach to the holding feature of an associated nasal septum holder. The nasal mask filter can have a pocket configured to attach to the holding feature. The pocket can be located at a middle part of the filter. The pocket can be opened on one end or on both ends like a tube. The pocket can exhibit various shapes and be specifically designed to accommodate and secure the holding feature. For example, the pocket could be a tubular pocket configured to wrap around a pin or cantilever located on the nasal septum holder. In specific embodiments, the pocket can include a seal which must be pierced to accommodate the holding feature. Such a feature will enable wearers to quickly distinguish used, and potentially contaminated, filters and unused filters. In specific embodiments, the seal can be pierced by tearing it away from an opening of the pocket. In specific embodiments, the seal can be pierced by the holding feature as the nasal mask filter is attached to the holding feature. In specific embodiments, the nasal mask filter can also include a vent, such as a one-way air vent to prevent the filter from being stressed during exhalation to assure the filter stays in place and maintains a seal with the wearer's skin.

In specific embodiments, the nasal mask filter can exhibit one or more features to enhance the hermeticity of the seal formed between the skin of the wearer and the filter. As an example of such a feature, an outer rim of the filter could contain a skin adhesive to enhance the fixation of the nasal filter mask on the wearer's nose. In specific embodiments, the adhesive component could be located on an outer border of a filter sheet of the filter. As another example of such a feature, the filter could include a wire rim on a portion of the outer border of the filter sheet or along the entire outer border of the filter sheet. The wire rim can be compressed after application of the filter to the nose of the wearer in order to form a firm seal with the wearer's nose. As another example of such a feature, the filter can include slits, such as one or more radial slits formed by scoring an outer edge of the filter. The slits can allow the outer rim of the filter to bend more easily to accommodate differently sized noses. The slits could be perforated and be separated to accommodate noses with sharper angles while remaining unseparated to provide a more consistent plane of material for noses with smoother angles that did not need the additional flexibility provided at that particular location.

Reference will be made to FIG. 1A and FIG. 1B, which are respectively a perspective view and a side view of a nasal mask according to an embodiment of this invention. The nasal mask 1 of the illustrated embodiment of the present invention includes a nasal septum holder and a nasal mask filter. The filter includes a filter sheet 20. The nasal septum holder includes a clamping body having a front middle section 11, and two clamping arms 12 and 13 that are bent inwardly and extend from both ends of the front middle section 11. The nasal septum holder also includes a holding feature 14 in the form of a pin, formed from the front wall of the front middle section 11. The two clamping arms are a right clamping arm 12 and a left clamping arm 13. The inner wall of the front middle section 11 and the side wall facing the right clamping arm 12 and the left clamping arm 13 are configures to be clamped at the front end of a user's nasal septum to hold the nasal mask 1 firmly fixed on the tip of the user's nose.

The filter sheet 20 of the present invention can be a unitary filter sheet with various portions or various independent portions attached together. The filter sheet can be a single continuous sheet to cover both nostrils with no perforations from sewing or other manufacturing processes within the plane of filtering that the nasal mask will be used for. As another example, the filter sheet can include a middle portion and two filter portions extending from both sides of the middle portions. The middle portion can be adapted to be anchored by the holding feature 14 so that the clamping body and the filter sheet 20 can be attached or detached. The filter sheet can completely cover the two nostrils and the surrounding skin of the user and can be used to filter the air inhaled by the user. In specific embodiments of the invention, a first filter portion is shaped to cover a front end of a nose without any perforations within the ambit of the nostrils. A pocket or other structure can be connected to the filter so that it can be attached to the holding feature proximate to the nasal septum of the nose. In this way, the nasal mask filter could cover part or all of the front end of the nose.

In specific embodiments of the invention, the nasal mask 1 can further include a skin adhesive component 30, which can be located at an outer rim of the filter sheet 20, to enhance the fixation of the nasal mask 1 on the nose of the user. The filter sheet and skin adhesive component can be configured to form a hermetic seal with the nose along the outer rim and to filter all air inhaled through the nose. The skin adhesive component 30 can be a material and/or element commonly used by those with ordinary knowledge in the art of the invention for adhering and fixing an object to the skin surface, which can be, but is not limited to, artificial leather, breathable adhesive tape, seamless tape, self-adhesive bandage, water activated adhesive paste, etc.

In the example of FIG. 1B, it is illustrated that the middle portion of the filter sheet 20 includes a downwardly opening pocket 21. In this example, the holding feature 14 is an upward structure in the form of a pin. The pocket 21 can accommodate the holding pin 14 so that the pocket, and therefore the filter sheet 20, can be anchored by that pin. Other configurations are possible in order for the holding pin to hold the filter sheet. For example, the holding pin could face downward or be vertically placed so that it can be attached to the filter sheet through an upper or side aperture on the filter sheet. The holding feature can comprise one or more prongs. The prongs can be used to provide additional strength to the connection between the nasal filter mask and the holding feature.

In specific embodiments of the present invention, the holding pin 14 of the clamping body can be made of a malleable material, so that the user can adjust the angle of the holding pin 14 according to usage requirements. The holding pin 14 may be, but is not limited to, a single upward bending structure, a single downward bending structure, or two structures bending to the left and right sides respectively.

In specific embodiments of the invention, the pocket 21 includes at least one opening to receive the holding pin 14, and the at least one opening can have a seal. When a user wants to use the filter sheet, the user could open the seal first before attaching the filter sheet to the holding pin. Alternatively, the seal could be pierced by the holding pin itself while the filter sheet is being attached thereto. The seal can be beneficial in that it can be easier for a user to determine if the filter has been used. If it is opened, it is most likely that it has been used.

Referring to FIG. 2, in an embodiment of the present invention, the right clamping arm 12 and the left clamping arm 13 are arcs inclined to the opposite side to provide the clamping body with elasticity. In this way, it can better fit the front end of the user's nasal septum. In specific embodiments of the invention, the pair of clamping arms form an arc with a maximum width of less than 50 centimeters. It is noted that the average human septum does not have a major degree of variation such that an elastic, and possibly magnetized, nasal septum holder can be nearly universally fit to a human nose without intense discomfort on the part of the wearer. However, the size of human nostrils can vary greatly. As such, minimizing the width, or lateral extent, of the nasal septum holder is important because the holder can otherwise block the free air flow out of the nose of the user and be counterproductive because wearers will be discouraged from breathing entirely through their noses. In another specific embodiment of the invention, the pair of clamping arms are elastic. In another specific embodiment of the present invention, the pair of clamping arms have an expanded spiral shape.

In an embodiment of the present invention, the clamping body is made of flexible and washable materials, so that it can be reused to reduce the waste of consumables. For example, the whole or part of the nasal septum holder can be reusable so that multiple filter sheets can be used while keeping the same nasal septum holder.

In an embodiment of the present invention, the clamping body can further include one or more protrusions 15. They can be respectively located at the distal ends of the right clamping arm 12 and the left clamping arm 13 to increase the area of contact, reduce pressure, and at the same time increase the friction of the contact surface, which can make the clamping body more firmly clamped to the user's nose. The protrusions 15 can have various functions such as providing a more comfortable fit by reducing pressure or covering harsh surfaces in the contact area. The protrusions 15 can also function as anti-dropping or anti-slipping pads. The material of the protrusions can be but is not limited to silicone, rubber, plastic, etc. In specific embodiments of the invention, the materials of the protrusions 15 do not cause irritation and do not absorb moisture.

An anti-dropping function for the clamping body can also be achieved by changing the shape of the two clamping arms, so that they stay in the nostrils more easily. For example, the clamping arms can be shaped in a zig zag or spiral shape so that they do not slide down easily. An anti-dropping mechanism can also be constructed with magnet or by shaping the clamping body to expand the nostrils. The protrusions 15 can include a magnet so they attract each other through the septum and stay fixed. This configuration could also help expand the nostrils and thus promote smoothness of the breathing. A similar effect could be achieved by providing a clamping body shaped to expand the nostrils.

In specific embodiments of the invention, the nasal septum holder 1 or at least the clamping body part can be used as a nose clip for snore reduction. As mentioned in the previous paragraph, certain configurations can help expand the nostrils and facilitate breathing, and therefore reduce snoring. The nasal septum holder or the clamping body of the present invention could then be worn separately or in combination with the filter for different purposes.

The filter sheet 20 can be of a single layer or multiple layers of suitable materials. The material can be selected in accordance with the intended use and level of protection of the nasal mask. The filter sheet 20 can contain at least one layer of fabric. For example the filter sheet 20 can contain at least one layer of melt-blown non-woven fabric. The fabric can be any fabric considered by those with ordinary knowledge in the field of the invention, that filters pollutant, viruses, dust, oil stains, suspended particles, droplets and other harmful substances, such as those announced by the United States: N100, N99, N95, R100, R99, R95, P100, P99, P95, or any other filter materials including cloth materials. as defined by the standard specifications for the classification of mask filter materials.

In an embodiment of the present invention, the nasal septum holder, the clamping body, the filter sheet 20, and/or the skin adhesive component 30 can be transparent or close to the color of the skin, so that the nasal mask 1 is less conspicuous and more appealing. However, other designs are perfectly acceptable. The nasal mask can be of any color or shape, and customizable. Since the filter sheet can be replaced, the users can use a variety of models by attaching filter sheets of different colors or shapes to the nasal septum holder. In a similar fashion, the nasal septum holder can be a of a variety of colors and shapes, for example to differentiate nasal septum holders of different users that live in the same house.

The protrusions 15 can be fixed features or replaceable features. For example, the protrusions can be replaced when they become worn. The protrusions 15 can be provided in a variety of sizes and shapes to fit different kinds of nose and users. For example, the user could decide to use a protrusion that has more padding if they like a more tightened fit. As another example, the protrusions can be provided as an extension of the clamping body and be of the same material.

Reference will now be made to FIG. 3, illustration of how specific embodiments of this invention can be used by a wearer. When using the nasal mask of this invention, including the nasal septum clip and the filter together, users can 1) open a seal of the filter if present, and anchor the filter to the holding pin in the clamping body of the nasal septum holder, 2) place the clamping body at the front end of the nasal septum with one clamping arm inside each of the nostrils and push the combined unit toward the nose, 3) press the border of the filter to the skin around the nostrils and let the skin adhesive component 30, if present, stick to the skin. This allows the unit to cover the entire front end of the nose and provides filtering function for all air-intake through the nose. Alternatively, the user can first place the clamping body in the nose, and then attach the filter to it. Therefore, the wearing method of the nasal mask 1 of this invention is intuitive and easy to operate. Once the nasal mask is on, with the anchoring clamping body and the adhesive component if provided, it stays on correctly and firmly, so that it provides continuous protection to the users.

In specific embodiments of the invention, the nose mask can have slits so that the filter sheet can be formed in various shapes to better fit the user's nose. With reference back to FIG. 1A, slit 31 is an example of this feature. They can be separable by the users to increase the flexibility of the filter for sharp angled noses or kept in place to provide a better seal for more curved noses.

Nasal Septum Clip

Specific embodiments of the invention refer to a nasal septum holder. The nasal septum holder can be the nasal septum holder of the nasal mask 1 described above with reference to FIGS. 1-3. The nasal septum holder can include a holding feature. The holding feature can be placed in the front middle section and be used to freely disassemble and assemble a nasal mask filter to increase the fixation of the nasal mask filter covering the opening of a user's two nostrils. The nasal septum holder can reduce the interferences of facial movements, and maintain the aesthetic appearance. The nasal septum holder can be used in conjunction with other masks when necessary. This design of the nasal septum clip can increase the continuous usage time of the mask and greatly increases the public's willingness to use it.

Specific embodiments of the invention provide a nasal septum holder including a clamping body, which has a front middle section and two clamping arms bent and extended inward from both ends of the front middle section. The clamping arms can reach into the user's nostrils and clamp on both sides of the nasal septum. The front middle section can have a holding feature, such as a holding pin, that can be for example perpendicular to the arms. The holding pin can be used to anchor a nasal mask filter for it to stay in place covering both nostrils and the surrounding skin of the user, as described above for the nasal mask of FIGS. 1-3.

In specific embodiments of the invention, the two clamping arms of the clamping body are respectively a right clamping arm and a left clamping arm forming an arc. In another specific embodiment of the present invention, the right clamping arm and the left clamping arm are in an inclined arc or u-shape to provide the elasticity.

In specific embodiments of the present invention, the clamping body further includes one or more protrusions, which can be respectively located at the ends of the two clamping arms. The protrusions can be the same or similar to the protrusions described above for the nasal mask 1 with reference to FIGS. 1-3. The protrusions can be anti-dropping pads. The anti-dropping mechanism can also be achieved by changing the shape of the clamping arms so that they stay inside the nose cavity without slipping.

In specific embodiments of the present invention, the nasal septum holder is adapted so that the nasal mask filter can be replaced with a face mask or a mouth nose mask or any other mask with a pocket to accommodate the holding pin.

In specific embodiments of the invention, the nasal septum holder includes a holding feature such as a holding pin. This configuration provides an anchor to the nasal mask filter. The filter can be assembled or disassembled at will. The holding feature allows the nasal mask filter to stay firmly covering the opening of the user's two nostrils. It can improve the stability, applicability and efficiency of the filter. It can also reduce the interference of the facial functions and improve aesthetics. This system can be used with or without other masks. Since it does not interfere with other facial functions, people don't have to take it off as often as they do with other kinds of masks. It could greatly increase the continuous protection for the public.

Reference will now be made to FIG. 4, which is a three-dimensional view of a nasal septum holder 100 according to specific embodiments of this invention. The nasal septum holder 100 includes a front middle section 110, and two clamping arms (120 and 130 respectively) bent inwardly from both ends of the front middle section 110. The front middle section 110 can include a holding feature, such as holding pin 140 on the front wall of section 110. The clamping body can be the same or similar to the clamping body described for the nasal mask 1 with reference to FIGS. 1-3. The front middle section 110 can be the same or similar to front middle section 11 described for the nasal mask 1 with reference to FIGS. 1-3. Arms 120 and 130 can be the same or similar to arms 12 and 13 described for the nasal mask 1 with reference to FIGS. 1-3. The pin 140 can be the same or similar to pin 14 described with reference to FIGS. 1-4.

The pin 140 can be constructed separately or as a single body or an extension of the nasal clip. In this way, pin 140 and the clamping body of the nasal septum holder 100 can be of the same or different materials. The pin and the clamping body can be separate pieces that can be attached together in various ways such as by welding, adhesive substances, screws, interlocking mechanisms, etc. The pin can be provided separately so that a user can use the clamping body separately for other purposes, such as reducing snoring, and attach the pin thereto for other purposes, such as wearing a filter sheet. In this way, the pin could be a separate structure that could be either permanently attached to the clamping body or detachably attached to the clamping body, so that the clamping body can be used with and without the pin. Alternatively, the pin and the clamping body can form a unitary structure. For example, the pin and clamping body could be molded together by a manufacturer, or could be two separate pieces that are combined together through a fusion process. In specific embodiments of the invention, the clamping body could be provided with a structure specially configured to receive a pin.

The two clamping arms can be a right clamping arm 120 and a left clamping arm 130, respectively. They can reach inside the user's nostrils. The inner wall of the front middle section 110, and the inner walls of the clamping arms 120, 130 can be shaped to surround the front portion of the user's nose septum.

Reference will now be made to FIG. 5A. FIG. 5A is a three-dimensional view of a nasal mask including a nasal mask filter 200 attached to a nasal septum holder 100 according to specific embodiments of the invention. The holding pin 140 of the nasal septum holder 100 of the present invention is used to install a nasal mask filter 200 so that it stabilizes the nasal mask filter 200 which covers the users' two nostrils. The nasal mask filter 200 can be changed at any time according to user's needs. The nasal mask filter 200 can be the same or similar to the one described for the nasal mask 1 with reference to FIGS. 1-3, and it can include a filter sheet, such as filter sheet 20, and an outer rim such as portion 30.

FIG. 5B is a side view of the nasal mask of FIG. 5A. In this example, the front middle portion of the nasal mask filter 200 is a pocket 210 that opens downward. Pocket 210 can be the same or similar to the pocket 21 described for the nasal mask 1 with reference to FIGS. 1-3. The holding pin 140 is a structure that is pointed upwards, and the pocket 210 has space to accommodate the holding pin 140. Alternatively, the pocket 210 can be a tube-like structure which opens on both ends or be open at the top if the pin faces downwards. Several configurations are possible so that the holding pin 140 can be attached to or accommodated within at least a portion of the filter 200.

In specific embodiments of the present invention, the holding pin 140 of the nasal septum holder 100 can be made of a malleable material, so that the user can adjust the angle of the holding pin 140. Further, the holding pin 140 can be, but is not limited to, a single upward bending structure, a single downward bending structure, two structures bending to the left and right sides, etc. The shape, length and width of holding pin 140 can be manufactured according to the scope of use. For example, in order to increase the clamping and fixing area with the nasal mask filter 200, the holding pin 140 can be flat and long. The length of the holding pin can be in accordance with the size of the filter or type of user. For example if the user is a kid the pin can be smaller. The shape of the pin can be as illustrated in the figures or different. For example, the pin can be a bended pin or otherwise have an irregular shape that fits a pocket designed for such irregular shape. The tip of the pin can be of a special shape or covered with a special material so that it does not cut, break or weakens the part of the filter in contact with it. The tip of the pin can also be shaped so that it pierces a seal of a filter sheet.

FIG. 6 is a top view of the nasal mask of FIG. 5A. In specific embodiments of the present invention, the right clamping arm 120 and the left clamping arm 130 are arcs inclined to the opposite side to form the clamping body. The clamping body can then be flexible, and can fit and stay at the front end of the user's nasal septum comfortably.

In specific embodiments of this invention, the nasal septum holder 100 can be made of elastic and washable materials, so that it can be reused and reduce the waste of consumables items.

In specific embodiments of the invention, the nasal septum holder 100 further includes two protrusions 150. The protrusions 150 can be the same or similar to the protrusions 15 disclosed for the nasal mask 1 with reference to FIGS. 1-3. The protrusions 150 can be anti-dropping pads 150. The protrusions 150 can be respectively located on the end of the right clamping arm 120 and the end of the left clamping arm 130. They can be used to increase the frictional force of the contact surface, so that the clamping body is more firmly held on the front end of the nose of the user. The protrusions 150 can be made of materials of common knowledge in the art, for example conventionally used anti-slipping materials. The material can be, but is not limited to, magnetic materials, silicone, rubber, plastic, etc. In specific embodiments of the invention, the material provides low irritation and low sensitivity. The protrusions 150 can be a special shape or form to stop the clamping body from slipping off the nose.

As explained before in this disclosure, when the anti-dropping mechanism is specifically constructed with magnet or when it's shaped to expand the nostrils, it can promote the smoothness of the breathing. In those embodiments, the nasal septum holder 100 can be used as a nose clip for snore reduction, In specific embodiments of the invention, the nasal septum holder 100 can be transparent or of a color close to the skin, so that the nasal septum holder 100 is less conspicuous and more beautiful. However, it can be designed and colored based on the market demands. For example, for the fun-loving crowd, it can be designed and colored to look like a snout.

FIG. 7 is an illustration of how the nasal mask of FIG. 5A can be used by a wearer. As explained for the nasal mask 1 with reference to FIGS. 1-3, the nasal septum holder 100 can anchor the nasal mask filter 200 via the holding pin 140. Users can use it the same or similar way as explained with reference to FIG. 3, for example by: 1) opening a seal in the filter if provided, anchoring the filter to the holding pin in the center of the clamping body, 2) placing the clamping body in front of the nasal septum with one clamping arm inside each of the nostrils and push the combined unit toward the nose, 3) pressing the edge of the filter to the skin around the nostrils and let the skin adhesive component, if provided, stick to the skin. As explained with reference to FIG. 3, the nasal septum holder could also be placed first and then the filter could be attached thereto.

In the specific embodiments of the invention where the nasal septum holder 100 includes the a holding feature such as holding pin 140, it can anchor the nasal mask filter to the right position, and allow easy installation and deinstallation of the nasal mask filter. It can also enable the mask to stay on correctly and for a prolonged period of time.

Nasal Mask Filter.

Specific embodiments of this invention refer to a nasal mask filter. The nasal mask filter can be the nasal mask filter of the nasal mask 1 described above with reference to FIGS. 1-3. The nasal mask filter can have the characteristics of small size, low interference, and high fixation. The design of the nasal mask filter can be both discreet and functional, which increases the continuous use time, so that, it greatly increases the public's willingness to use the nasal mask filter. The nasal mask filter can be easily replaced to improve hygiene and practicality. Because of its size, the waste of filter materials can be reduced and it is easy to carry. The nasal mask filter can be used by itself or in conjunction with other facial masks if necessary.

In specific embodiments of the invention, the nasal mask filter can include 3 sections: a middle section, and a left and a right sections. The middle section can include a pocket or tube, that can be used to accommodate the holding pin of the nasal septum holder. The entire filter can be used to cover the two nostrils and the surrounding skin of a user. The nasal mask filter can include a first filter portion shaped to cover a first half of a front end of a nose, a second filter portion shaped to cover a second half of the front end of the nose and a pocket connected to the first and second filter portions. The nasal mask filter can be shaped to cover the front end of the nose when the pocket is attached to a holding feature proximate a nasal septum of the nose.

In specific embodiments of the present invention, the nasal mask filter filters the air flowing through the nasal mask filter.

In specific embodiments of the present invention, the nasal mask filter further includes a skin adhesive component. The skin adhesive component can be a skin adhesive material. It can be located on the outer rim of the nasal mask filter. It can be used to strengthen the fixation of the nasal mask filter on the nose of the user, so that the mask stays firmly over the nostrils and their surrounding skin. In specific embodiments of the present invention, the skin adhering component is a strap or a clamp.

The use of the skin adhering component, if provided, allows the nasal mask filter of the invention to be tightly fixed on the front end of the nose of the user and remain in place while a user is exhaling. It is not easy to move, and can be used with the nasal septum holder at the same time to further strengthen the fixation of the nasal mask filter. The nasal mask filter of the present invention can therefore be used via the skin attaching component alone, the holding feature of the nasal septum holder alone, or both.

In specific embodiments of the invention, the outer rim of the filter is formed by a malleable wire. The filter can be adjusted by adjusting the malleable wire to the contour of the face and or nose. In this way, the malleable wire can help the filter to stay in place and can also contribute to creating a sealed environment once the user has adjusted the wire. In specific embodiments, the malleable wire can be the skin adhesive component.

In specific embodiments of the present creation, the middle part of the nasal mask filter is a pocket, open on one end, or a tube, open on both ends.

In specific embodiments of the present invention, the pocket or tube accommodates a holding feature, as described before in this disclosure.

In specific embodiments of the present invention, the nasal mask filter may further include a vent to reduce the air resistance through the nasal mask filter. The vent can be a one-way vent that allows air to flow in one direction so that the user can exhale comfortably but the air is still filtered when inhaling.

In specific embodiments of the invention, the nasal mask filter can be used on the nose of humans or animals. In specific embodiments of the invention, the nasal mask filter can be used with a face mask or other types of masks if needed.

Reference will be made to FIG. 8, which is a 3-dimensional view of a nasal mask filter 300 according to specific embodiments of the invention. The nasal mask filter 300 can include a filter sheet 310, and the filter sheet 310 can have a middle part and two parts on each side of the middle part. The filter can cover the entire front portion of the user's nose, including his nostrils, so that it filters the air inhaled by the user. The nasal mask filter 300 and the filter sheet 310 can be the same or similar to the nasal mask filter and the filter sheet described for the nasal mask 1 and the nasal septum holder 100 with reference to FIGS. 1-7.

The nasal mask filter 300 of the present invention may further include a skin adhesive component 320 to enhance the fixation of the nasal mask filter 300 on the user's nose. The skin adhesive component can be the same or similar to the skin adhesive component described for the nasal mask 1 and the nasal septum holder 100 with reference to FIGS. 1-7. The skin adhesive component can be placed around the filter sheet, over or under the filter sheet, or in any other part of the filter such as on one or each side. The skin adhesive component can be any portion that attaches to the skin by for example the use of an adhesive substance. The surface that includes the skin attaching component can be covered when the filter has not been used so that the user can uncover it when the filter is going to be used, for example by ripping out a protective layer of material that uncovers the skin attaching component. The skin attaching component can be optionally added to the filter for example via a double-sided adhesive tape or any other attaching means such as snaps or hook and loop mechanisms.

In specific embodiments of the invention, the skin adhesive component 320 includes but is not limited to a breathable tape, artificial leather, breathable tape, seamless tape, self-adhesive bandage, bandage, water-activated adhesive, fixtures, etc. It can be located on the outer rim of the filter sheet 310 or anywhere else on the filter sheet, for example to the sides of the filter sheet. In specific embodiments of the invention, the skin adhesive component is provided separately, and it can be placed over the filter sheet once the filter is placed on the nose.

The skin adhering component 320 can have a wider structure at a position corresponding to the nose of the user, so that the nasal mask filter 300 of the present invention can be more widely applied to different shapes of noses.

Furthermore, the skin adhering component 320 can include several slits 321 at different positions corresponding to the nose, for example between the top of the nose and the wings of the nose, so that the skin adhesive component 320 can be adjusted to match different shapes of the noses. The filter could include a set of scored portions formed on an outer rim of the filter that form a set of slits when separated. The slits 321 can be in the form of wrinkles on the material so that the filter fits different sizes and shapes by stretching the wrinkles. All these self-adjustment designs are meant to assist users to adjust the filter to fit his own needs so that his nostrils can be totally protected.

Reference will be made to FIG. 9A, which illustrates a three-dimensional view of a nasal mask including a nasal mask filter 300, with a vent, attached to a nasal septum holder according to specific embodiments of this invention. The front middle section of the nasal mask filter 300 is assembled with a holding pin 331 of a nasal septum holder 330, so that the nasal mask filter 300 of the present invention and the nasal septum holder are assembled. The filter part is anchored by the holding pin on the nasal septum holder 330. They can be assembled and disassembled freely, so that users can replace the filter mask unit when necessary. The nasal septum holder 330, filter 300 and holding pin 331 can be the same or similar to the nasal septum holder, filter and holding features described with reference to FIGS. 1-8.

FIG. 9B is a side view of the nasal mask of FIG. 9A. The front middle portion of the filter sheet 310 of the nasal mask filter 300 is illustrated as a pocket 311 with an opening in the bottom, and the holding pin 331 is an upwards bent structure. The pocket 311 and filter sheet 310 can be the same or similar to the pocket and filter sheet described with reference to FIGS. 1-8. The pocket 311 has space for accommodating the holding pin 331 as explained before in this disclosure.

In specific embodiments of the present invention, the pocket 311 has a sealed opening. In those embodiments, when using the nasal mask filter 300, the opening can be unsealed and then connected to the holding pin 331 to be anchored. In this way, it is easy to judge whether the nasal mask filter 300 of this invention has been used according to whether the seal has been opened.

In specific embodiments of the present invention, the filter sheet 310 may further include a vent 312. It may be, but is not limited to, a strip structure. It can be used to reduce the air resistance of the exhalation and to enhance airflow. The vent 312 may be composed of materials and/or structures that are commonly used by those with ordinary knowledge in the art to increase the ventilation rate, such as an exhalation one-way valve.

According to specific embodiments of the present invention, the filter sheet 310 can be, but is not limited to, a single-layer fabric or a multi-layer fabric composition. The fabric can be any fabric used by those with ordinary knowledge in the art, used for filtering pollutant toxins such as viruses, dust, oil stains, suspended particles, droplets, etc. These fabrics can be N100, N99, N95, R100, R99, R95, P100, P99, P95, or any other filter materials including cloth materials. and others, as defined in the standard specifications for the classification of mask filter materials announced by the United States. In an embodiment of the present invention, the filter sheet 310 contains at least one layer of melt blown non-woven fabric.

In specific embodiments of the invention, the filter sheet 310 and the skin adhesive component 320 are transparent or close to the color of the skin, so that the nasal mask filter 300 of the invention is less conspicuous and more beautiful. It can also accommodate designs, like a snout, to imitate a friendly animal looking face to make it a fun thing to wear. This can appeal to young-at-heart type of users.

FIG. 10 is a top view of the nasal mask filter of FIG. 9A. It illustrates the parts of the nasal mask described herein. In specific embodiments of the invention, the pocket 311 can be a different structure shaped to accommodate the pin. For example it can be a matching hook for pin 331 or a similar structure that is attached to the filter sheet to that the holding pin can be attached thereto, made of the same or different material than the filter sheet. For example, the structure can be a silicon, metallic or plastic loop on the filter sheet.

Reference will be made to FIG. 11, which is an illustration of how the nasal mask of FIG. 9A can be used by a wearer. When the nasal mask filter 300 is used, the filter sheet 310 can cover the openings of the two nostrils, and the skin adhesive component 320 can be attached to the skin of the nose surrounding the nostrils. Alternatively or in combination, the filter sheet can also by affixed and/or adjusted via a the malleable wire described before. When nasal mask filter 300 of the present invention is anchored by the nasal septum holder 330, it would be much more firmly fixed to position on the nose.

The wearing method of the nasal mask filter of the present invention is intuitive and easy to operate, and it can be easily replaced to improve hygiene. The use of the skin adhesive component 320 can make the nasal mask filter 300 of the present invention less disturbing. It can be tightly fixed on the front end of the user's nose without being easily moved. The nasal septum holder 330 can be used in conjunction with it to further enhance the stability of the nasal mask filter. Therefore, the nasal mask filter 300 can have the characteristics of convenient to wear, easy to carry, and good stability, less intrusive to the facial functions, which can greatly increase people's willingness to use. It is especially suitable for people who do not like to wear big masks. The nasal mask filter 300 of this creation can be used alone or with other masks or masks.

The wearing method of the nasal mask filter of this invention is intuitive. The filter is easy to operate and can be easily replaced to improve hygiene. Therefore, the nasal mask filter of this invention is convenient to wear, easy to carry, and replace. It can greatly increase people's willingness to use a nose filter or mask. The nasal mask filter of this invention can be used alone or in combination with other masks.

While the specification has been described in detail with respect to specific embodiments of the invention, it will be appreciated that those skilled in the art, upon attaining an understanding of the foregoing, may readily conceive of alterations to, variations of, and equivalents to these embodiments. Although examples in the disclosure were given with reference to specific embodiments and figures, features from different embodiment can be combined with each other or removed to obtain different combinations of features. The different elements of the nasal mask described with reference to different figures throughout this disclosure, such as the nasal septum holder, the nasal mask filter, the filter sheet, the skin adhesive component, slits, protrusions, clamping body, etc. can be the same or similar elements, and have the same or similar characteristics, throughout the different figures and embodiments disclosed. These and other modifications and variations to the present invention may be practiced by those skilled in the art, without departing from the scope of the present invention, which is more particularly set forth in the appended claims.

What is claimed is:

1. A nasal mask comprising:
a clamping body with a pair of clamping arms, wherein the clamping body and the pair of clamping arms are shaped to surround a nasal septum;
a holding feature attached to the clamping body;
a filter with a pocket or a tube;
wherein the filter is shaped to cover a front end of a nose when the holding feature is attached to the pocket
wherein the pocket has a seal; and
the seal is pierced for the pocket to be placed on the holding feature.

2. The nasal mask of claim 1, wherein:
the holding feature is a cantilever; and
the pocket is centrally located on the filter.

3. The nasal mask of claim 1, wherein:
the holding feature includes an adhesive.

4. The nasal mask of claim 1, wherein the filter further comprises:
a malleable wire forming an outer rim of the filter.

5. The nasal mask of claim 1, wherein the filter further comprises:
a skin adhesive component located on an outer rim of the filter.

6. The nasal mask of claim 5, wherein the filter further comprises:
a filter sheet which includes the outer rim; and
wherein the filter sheet and skin adhesive component are configured to form a hermetic seal with the nose along the outer rim and to filter all air inhaled through the nose.

7. The nasal mask of claim 1, wherein the filter further comprises:
a filter sheet; and
a set of slits in an outer rim of the filter sheet.

8. The nasal mask of claim 1, wherein:
the filter includes a set of scored portions formed on an outer rim of the filter; and
the set of scored portions form a set of slits when separated.

9. The nasal mask of claim 1, wherein:
the pocket is tubular; and
the pocket is centrally located on the filter.

10. The nasal mask of claim 1, further comprising:
a first protrusion located at a first distal end of the pair of clamping arms; and
a second protrusion located at a second distal end of the pair of clamping arms.

11. The nasal mask of claim 10, wherein:
the pair of clamping arms are elastic; and
the first protrusion and the second protrusion are pads.

12. The nasal mask of claim 1, wherein:
the holding feature is a cantilever; and
the pocket is placed on the holding feature.

13. The nasal mask of claim 1, wherein:
the pair of clamping arms form one of an arc and a u-shape; and
the pair of clamping arms are elastic.
14. The nasal mask of claim 1, wherein:
the holding feature is attached to a malleable portion of the clamping body.
15. The nasal mask of claim 1, wherein:
the holding feature bends upward from the clamping body towards the pair of clamping arms.
16. The nasal mask of claim 1, wherein:
the holding feature comprises at least two prongs.
17. The nasal mask of claim 1, wherein:
the pair of clamping arms have an expanded spiral shape.
18. The nasal mask of claim 1, wherein:
the pair of clamping arms form an arc with a maximum width of less than 50 centimeters.
19. The nasal mask of claim 1, wherein:
the filter includes a one-way vent.
20. A nasal septum holder for a nasal mask, the nasal septum holder comprising:
a clamping body;
a pair of clamping arms, wherein the clamping body and the pair of clamping arms are shaped to surround a nasal septum;
a holding feature configured to be attached to the clamping body;
wherein the holding feature is shaped to attach to a pocket in a filter;
the holding feature bends upward from the clamping body towards the pair of clamping arms.
21. The nasal septum holder of claim 20, wherein:
the holding feature is a cantilever.
22. The nasal septum holder of claim 20, further comprising:
a first protrusion located at a first distal end of the pair of clamping arms; and
a second protrusion located at a second distal end of the pair of clamping arms.
23. The nasal septum holder of claim 22, wherein:
the pair of clamping arms are elastic; and
the first protrusion and the second protrusion are pads.
24. The nasal septum holder of claim 20, wherein:
the pair of clamping arms form one of an arc and a u-shape; and
the pair of clamping arms are elastic.
25. The nasal septum holder of claim 20, wherein:
the holding feature is attached to a malleable portion of the clamping body.
26. The nasal septum holder of claim 20, wherein:
the holding feature comprises at least two prongs.
27. The nasal septum holder of claim 20, wherein:
the pair of clamping arms have an expanded spiral shape.
28. The nasal septum holder of claim 20, wherein:
the pair of clamping arms form an arc with a maximum width of less than 50 centimeters.
29. A nasal mask filter comprising:
a filter shaped to cover a front end of a nose;
a pocket connected to the filter;
wherein the filter is shaped to cover the front end of the nose when the pocket is attached to a holding feature proximate a nasal septum of the nose,
wherein the pocket has a seal; and
the seal is pierced for the pocket to be placed on the holding feature.
30. The nasal mask filter of claim 29, wherein:
the pocket is centrally located on the nasal mask filter.
31. The nasal mask filter of claim 29, further comprising:
a malleable wire forming an outer rim of the nasal mask filter.
32. The nasal mask filter of claim 29, further comprising:
a skin adhesive component located on an outer rim of the nasal mask filter.
33. The nasal mask filter of claim 32, further comprising:
a filter sheet which includes the outer rim; and
wherein the filter sheet and skin adhesive component are configured to form a hermetic seal with the nose along the outer rim and to filter all air inhaled through the nose.
34. The nasal mask filter of claim 29, further comprising:
a filter sheet; and
a set of slits in an outer rim of the filter sheet.
35. The nasal mask filter of claim 29, further comprising:
a set of scored portions formed on an outer rim of the nasal mask filter, and
wherein the set of scored portions form a set of slits when separated.
36. The nasal mask filter of claim 29, wherein:
the pocket is tubular; and
the pocket is centrally located on the nasal mask filter.
37. The nasal mask filter of claim 29, further comprising:
a one-way vent.

* * * * *